US005952376A

United States Patent [19]
Smith, III et al.

[11] Patent Number: 5,952,376
[45] Date of Patent: Sep. 14, 1999

[54] TRIENYL COMPOUNDS

[75] Inventors: Amos B. Smith, III, Merion; Qiyan Lin, Philadelphia, both of Pa.

[73] Assignee: The Trustees of the University of Pennsylvania, Phialdelphia, Pa.

[21] Appl. No.: 08/966,428

[22] Filed: Nov. 7, 1997

[51] Int. Cl.[6] .......................... A61K 31/35; A61K 31/38; A61K 31/445; C07D 309/10

[52] U.S. Cl. .......................... 514/460; 514/326; 514/327; 514/328; 514/432; 546/208; 546/214; 546/243; 549/13; 549/78; 549/417; 549/423; 549/428

[58] Field of Search ..................................... 546/243, 208, 546/214; 514/326, 327, 328, 432, 460; 549/13, 417, 423, 428

[56] References Cited

U.S. PATENT DOCUMENTS

| | | | |
|---|---|---|---|
| 5,328,929 | 7/1994 | Pettit et al. | 514/462 |
| 5,393,897 | 2/1995 | Pettit et al. | 549/267 |
| 5,436,400 | 7/1995 | Pettit et al. | 549/267 |

OTHER PUBLICATIONS

Evans DA et al. Tetrahedron Letters. 39(13), 1709–1712, 1998.

Akiyama et al., "Total Synthesis and Absolute Configuration of (–)—Sedacryptine", *Synlett*, 1996, 100–102.

Bai, R. et al., "The Spongistatins, Potently Cytotoxic Inhibitors of Tubulin Polymerization, Bind in a Distinct Region of the Vinca Domain", *Biochem.*, 1995, 34 , 9714–9721.

Claffey, M.M. et al., "A Method for Constructing the C2–C12 Dispiroacetal Moiety of Altohyrtin A", *J. Org. Chem.*, 1996, 61, 7646–7647.

Dale, J.A. et al., "Nuclear Magnetic Resonance Enantiomer Reagents. Configurational Correlations via Nuclear Magnetic Resonance Chemical Shifts of Diastereomeric Mandelate, 0–Methylmandelate, and α–Methloxy–α–Trifluoromethyphenylacetate (MTPA) Esters[1,2]"*J. Am. Chem. Soc.*, 1973, 95, 512–519.

De Lima, C. et al., "Reaction of α–Sulfonyl Carbanions with Electrophilic Monohalogenocarbenoids: A New Wittig–Like Formation of Alkenes", *Synlett*, 1992, 133–134.

Dess, D.B. et al., "Readily Accessible 12–I–5[1]Oxidant for the Conversion of Primary and Secondary Alcohols to Aldehydes and Ketones", *J. Org. Chem.*, 1993, 48, 4155–4156.

Fusetani, N. et al., "Cinachyrolide A: A Potent Cytotoxic Macrolide Possessing Two Spiro Ketals from Marine Sponge *Cinachyra sp.*[1]", *J. Am. Chem. Soc.*, 1993, 115, 3977–3981.

Hayes, C.J. et al., "A Method for Constructing the C18–C28 Dispiroacetal Moiety of Altohyrtin A",*J. Org. Chem.*, 1997, 62, 2678–2679.

Hosokawa, S. et al., "Partial Synthesis of Ciguatoxin, an A/B/C Fragment", *Synlett*, 1996, 351–352.

Ireland, R.E. et al., "An Improved Procedure for the Preparation of the Dess–Martin Periodinane", *J. Org. Chem.*, 1993, 58, 2889.

Kobayashi, M. et al., "Absolute Stereostructures of Altohyrtin A and Its Congeners, Potent Cytotoxic Macrolides from the Okinawan Marine Sponge *Hyrtios altum*", *Tetra. Lett.*, 1994, 35(8), 1243–1246.

Kobayashi, M. et al., "Altohyrtin A, a Potent Anti–tumor Macrolide from the Okinawan Marine Sponge *Hyrtios altum*", *Tetrahedron Lett.*, 1993, 34 (17), 2795–2798.

Kobayashi, M. et al., "Marine Natural Products. XXXVIII. [1)] Absolute Stereostructures of Altohyrtins A, B, and C and 5–Desacetylaltohyrtin A, Potent Cytotoxic Macrolides, from the Okinawan Marine Sponge *Hyrtios altum*", Chem. Pharm. Bull., 1996, 44 (11), 2142–2149.

Paquette, L.A. et al., "A Modular Approach to Marine Macrolide Construction. 1. An Enantiocontrolled Route to the C1–C12 (AB) Spiroacetal Sector", *Tetra. Lett.*, 1996, 38(29), 5115–5118.

Paquette, L.A. et al., "A Modular Approach to Marine Macrolide Construction. 2. Concise Stereocontrolled Synthesis of the C17–C28 (CD) Spiroacetal Component", Tetra. Lett., 1997, 38 (29), 5119–5122.

Paterson, I. et al., "Studies in Marine Macrolide Synthesis: Stereocontrolled Synthesis of the AB–Spiroacetal Subunit of Spongistatin 1 (Altohyrtin A)", *Tetra. Lett.*, 1996, 37(47), 8581–8584.

Paterson, I. et al., "Studies in Marine Macrolide Synthesis: Stereocontrolled Synthesis of the F–Ring Subunit of Spongistatin 1 (Altohyrtin A)", *Tetra. Lett.,* 1997, 38(32), 5727–5730.

Pettit, G.R. et al., "Isolation and Structure of Spongistatin $1^{1a}$", *J. Org. Chem.,* 1993, 58, 1302–1304.

Pettit, G.R. "Marine animal and terrestrial plant anticancer constituents$^a$", *Pure & Appl. Chem.,* 1994, 66(10/11), 2271–2281.

Pornet, J., "Action Du Propargyltrimethylsilane Sure Les Derives Carbonyles En Presence De Tetrachlorure De Titane: Nouvelle Voie D'Acces Aux Derives Chloropreniques", *Tetrahedron Lett.,* 1981, 22, 253–254 (Summary in English).

*Primary Examiner*—Evelyn Mei Huang
*Attorney, Agent, or Firm*—Woodcock Washburn Kurtz Mackiewcz & Norris LLP

[57] ABSTRACT

Triene-containing compounds which mimic the chemical and/or biological activity of the spongistatins are provided, as are methods and intermediates useful in their preparation.

14 Claims, 3 Drawing Sheets

TRIENYL COMPOUNDS

GOVERNMENT SUPPORT

Certain of the inventors were supported by National Institutes of Health Grant CA-70329.

FIELD OF THE INVENTION

This invention relates to triene-substituted compounds, to pharmaceutical compositions containing them, and to methods and intermediates useful in their preparation.

BACKGROUND OF THE INVENTION

The spongipyrans, a new family of sponge metabolites available only in minute quantities, appear to be the most potent inhibitors of cancer cell growth discovered to date. Pettit, et al., described the first examples, spongistatins, in 1993 (Pettit, et al., *J. Org. Chem.* 1993, 58, 1302) and subsequently isolated congeners thereof (Pettit, *Pure & Appl. Chem.* 1994, 66, 2271). Spongistatin 1 (1, FIG. 1), the most abundant compound, proved to be active against several chemoresistant tumor types, including human melanoma and lung, colon, and brain cancers, with $GI_{50}$'s of $2.5–3.5\times10^{-11}$ M (see, e.g., Bai, et al., *Biochemistry* 1995, 34, 9714). Further investigators revealed that 1 inhibits mitosis by binding to tubulin and blocking microtubule assembly. Other sponges produce cinachyrolide A and the altohyrtins A-C, isolated by the Fusetani (see, Fusetani, et al., *J. Am. Chem. Soc.* 1993, 115, 3977), and Kitagawa groups (see, Kobayashi, et al., *Tetrahedron Lett.* 1993, 34, 2795; Kobayshi, et al., *Tetrahedron Lett.* 1994, 35, 1243; Kobayashi, et al., *Chem. Pharm. Bull.* 1996, 44, 2142). These substances likewise display cytotoxicity against cancer cell lines but, likewise, are difficult to obtain from natural sources yet are structurally complex and, thus, difficult to synthesize.

There is, therefore, a need for improved synthetic methods and/or less complex compounds having similar levels of cytotoxicity.

OBJECTS OF THE INVENTION

It is one object of the present invention to provide compounds which mimic the chemical and/or biological activity of the spongistatins.

It is a further object to provide compositions having antitumor activity comprising such compounds.

It is another object to provide processes for the preparation of such compounds.

It is yet another object of this invention to provide intermediates useful in such processes.

SUMMARY OF THE INVENTION

These and other objects are satisfied by the present invention, which provides triene-containing compounds which mimic the chemical and/or biological activity of the spongistatins. In preferred embodiments, such compounds have formula I:

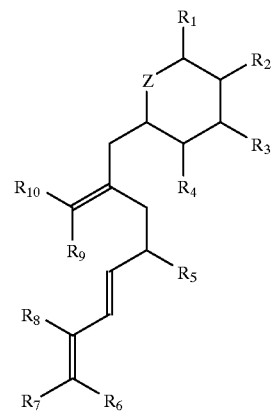

wherein:

Z is O, S or NR' where R' is H or $C_1$–$C_6$ alkyl;

$R_1$ is H, $C_1$–$C_{10}$ alkyl, =O, or $OR_A$ wherein $R_A$ is H, $C_1$–$C_{10}$ alkyl, $C_6$–$C_{14}$ aryl, $C_7$–$C_{15}$ arylalkyl, or an acid labile hydroxyl protecting group;

$R_2$, $R_3$, and $R_4$ are, independently, H, $C_1$–$C_{10}$ alkyl, or $OR_B$ wherein each $R_B$ is, independently, H, $C_1$–$C_{10}$ alkyl, $C_6$–$C_{14}$ aryl, $C_7$–$C_{15}$ arylalkyl, or an acid labile hydroxyl protecting group;

$R_5$ is H, $C_1$–$C_{10}$ alkyl, =O, or $OR_C$ wherein $R_C$ is H, $C_1$–$C_{10}$ alkyl, $C_6$–$C_{14}$ aryl, $C_7$–$C_{15}$ arylalkyl, or an acid labile hydroxyl protecting group;

$R_6$, $R_7$, $R_9$, and $R_{10}$ are, independently, H, F, Cl, Br, I, or $CH(R_D)(R_E)$ where:

$R_D$ is H, $C_1$–$C_{10}$ alkyl, $OR_F$, or =O;

$R_E$ is $OR_F$ or —$CH_2$—$R_F$;

$R_F$ is $C_6$–$C_{14}$ aryl, tetrahydropyranyl, furanosyl, pyranosyl, $C_3$–$C_{10}$ lactonyl or 2-pyranonyl; and $R_8$ is H, F, Cl, Br, or I.

The present invention also provides methods for inhibiting mammalian cell proliferation by contacting mammalian cells with a compound according to the invention or by administering a compound according to the invention (or a pharmaceutical composition comprising such a compound) to a mammal suffering from undesired cell proliferation.

BRIEF DESCRIPTION OF THE DRAWINGS

The numerous objects and advantages of the present invention may be better understood by those skilled in the art by reference to the accompanying figures, in which.

DETAILED DESCRIPTION OF THE PREFERRED EMBODIMENTS

Figure 1:
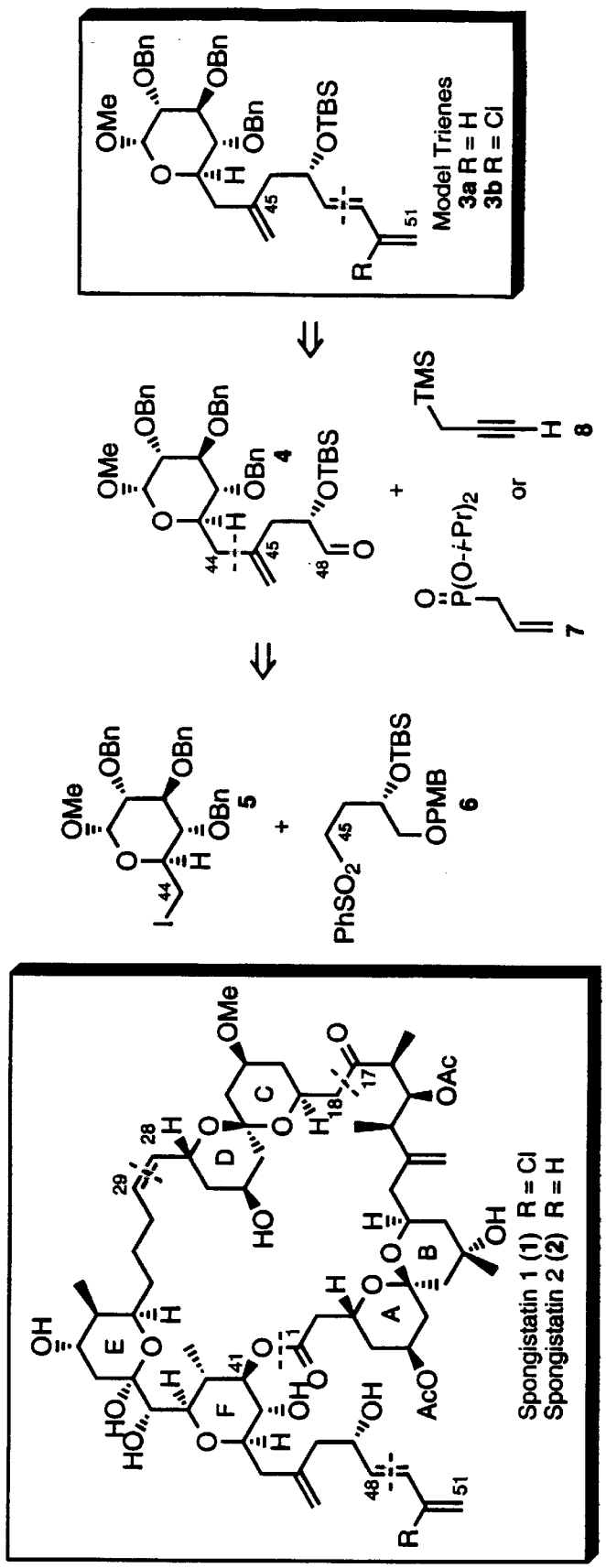
FIG. 1 shows spongistatins 1 and 2 and a retrosynthetic analysis for compounds 3a and 3b.

The present invention provides compounds which mimic the chemical and/or biological activity of the spongistatins. In preferred embodiments, such compounds have formula I:

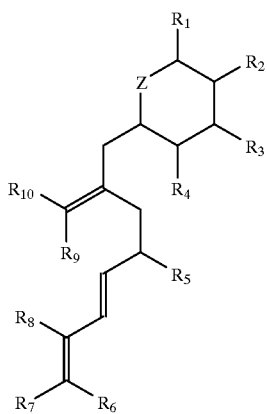

wherein:

Z is O, S or NR' where R' is H or $C_1-C_6$ alkyl;

$R_1$ is H, $C_1-C_{10}$ alkyl, =O, or $OR_A$ wherein $R_A$ is H, $C_1-C_{10}$ alkyl, $C_6-C_{14}$ aryl, $C_7-C_{15}$ arylalkyl, or an acid labile hydroxyl protecting group;

$R_2$, $R_3$, and $R_4$ are, independently, H, $C_1-C_{10}$ alkyl, or $OR_B$ wherein each $R_B$ is, independently, H, $C_1-C_{10}$ alkyl, $C_6-C_{14}$ aryl, $C_7-C_{15}$ arylalkyl, or an acid labile hydroxyl protecting group;

$R_5$ is H, $C_1-C_{10}$ alkyl, =O, or $OR_C$ wherein $R_C$ is H, $C_1-C_{10}$ alkyl, $C_6-C_{14}$ aryl, $C_7-C_{15}$ arylalkyl, or an acid labile hydroxyl protecting group;

$R_6$, $R_7$, $R_9$, and $R_{10}$ are, independently, H, F, Cl, Br, I, or $CH(R_D)(R_E)$ where:

$R_D$ is H, $C_1-C_{10}$ alkyl, $OR_F$, or =O;

$R_E$ is $OR_F$ or —$CH_2$—$R_F$;

$R_F$ is $C_6-C_{14}$ aryl, tetrahydropyranyl, furanosyl, pyranosyl, $C_3-C_{10}$ lactonyl or 2-pyranonyl; and $R_8$ is H, F, Cl, Br, or I.

In particularly preferred embodiments: Z is O; $R_1$ is $OR_A$ wherein $R_A$ is H or $C_1-C_{10}$ alkyl; $R_2$, $R_3$, and $R_4$ are, independently, $C_1-C_{10}$ alkyl or $OR_B$ wherein each $R_B$ is, independently, H or $C_7-C_{15}$ arylalkyl; $R_5$ is $OR_C$ wherein $R_C$ is H or an acid labile hydroxyl protecting group; $R_6$, $R_7$, $R_9$, and $R_{10}$ are, independently, H; and/or $R_8$ is H or Cl.

Alkyl groups according to the invention include but are not limited to straight chain and branched chain hydrocarbons such as methyl, ethyl, propyl, pentyl, isopropyl, 2-butyl, isobutyl, 2-methylbutyl, and isopentyl moieties having 1 to about 10 carbon atoms, preferably 1 to about 6 carbon atoms. Alkyl groups according to the invention optionally can be unsubstituted or can bear one or more substituents such as, for example, halogen hydroxyl, amine, and epoxy groups.

Aryl groups according to the invention are aromatic and heteroaromatic groups having 6 to about 14 carbon atoms, preferably from 6 to about 10 carbon atoms, including, for example, naphthyl, phenyl, indolyl, and xylyl groups and substituted derivatives thereof, particularly those substituted with amino, nitro, hydroxyl, methyl, methoxy, thioimethyl, trifluoromethyl, mercaptpyl, and carboxy groups. Alkaryl groups are groups that contain alkyl and aryl portions and are covalently bound to other groups through the alkyl portion, as in a benzyl group.

Protecting groups are known per se as chemical functional groups that can be selectively appended to and removed from functionality, such as hydroxyl and amine groups, present in a chemical compound to render such functionality inert to certain chemical reaction conditions to which the compound is exposed. See, e.g., Greene and Wuts, Protective Groups in Organic Synthesis, 2d edition, John Wiley & Sons, New York, 1991. Numerous hydroxyl protecting groups are known in the art, including the acid-labile t-butyldimethylsilyl, diethylisopropylsilyl, and triethylsilyl groups and the acid-stable aralkyl (e.g., benzyl), triisopropylsilyl, and t-butyldiphenylsilyl groups.

Certain compounds of the invention contain amino groups and, therefore, are capable of forming salts with various inorganic and organic acids. Such salts are also within the scope of this invention. Representative salts include acetate, adipate, benozate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, priopionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

In our unified approach to the spongistatins, the labile C(48-51) conjugated diene moiety of the side-chain will be introduced at the end of the synthesis. As shown in FIG. 1, our initial targets were trienes 3a and 3b, in which a D-glucosyl moiety is believed to mimic the C(39-43) F-ring pyran. Triene 3a, which contains the unsubstituted diene of spongistatin 2, can be generated by Horner-Emmons olefination of the C(48) aldehyde derived from 4 with diisopropyl allylphosphonate 7. The chlorinated diene in 3b, the model for spongistatin 1, can be produced from the same aldehyde upon treatment with propargyltrimethylsilane 8 and $TiCl_4$, generally according to the method of Pornet (see, e.g., Pornet, Tetrahedron Lett. 1981, 22, 453). Precursor 4 in turn can be prepared via coupling of iodide 5 (see, e.g., Hosokawa, et al., Synlett 1996, 351) with sulfone 6 (see, e.g., Akiyama, et al., Synlett 1966, 100) followed by Julia methylenation (see, e.g., De Lima, et al., Synlett 1992, 133).

Figure 2:
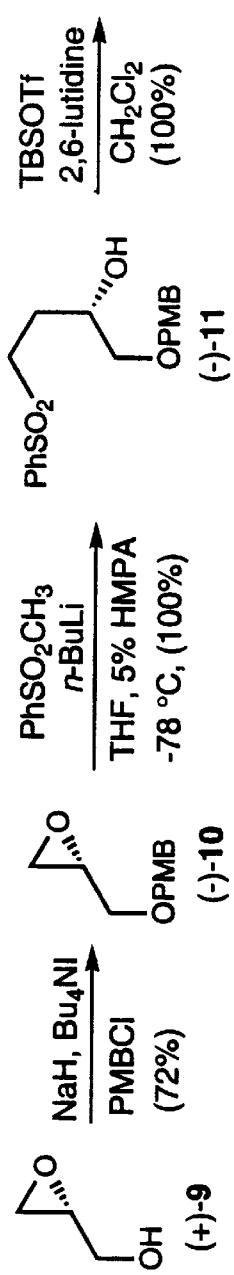
FIG. 2 shows a synthetic scheme for compound 6.

As shown in FIG. 2, sulfone (−)-6 was obtained in three steps from commercially available (R)-(+)glycidol [(+)-9]. Protection as the p-methoxybenzyl (PMB) ether (NaH, $Bu_4NI$, PMBCl; 72% yield) and quantitative epoxide opening with the lithio derivative of methyl phenyl sulfone furnished (−)-11; the absolute configuration was confirmed by Mosher analysis (see, e.g., Dale, et al., J. Am. Chem. Soc. 1973, 95, 512). Silylation (TBSOTf, 2,6-lutidine, $CH_2Cl_2$; 100%) then completed the synthesis of (−)-6.

Figure 3:
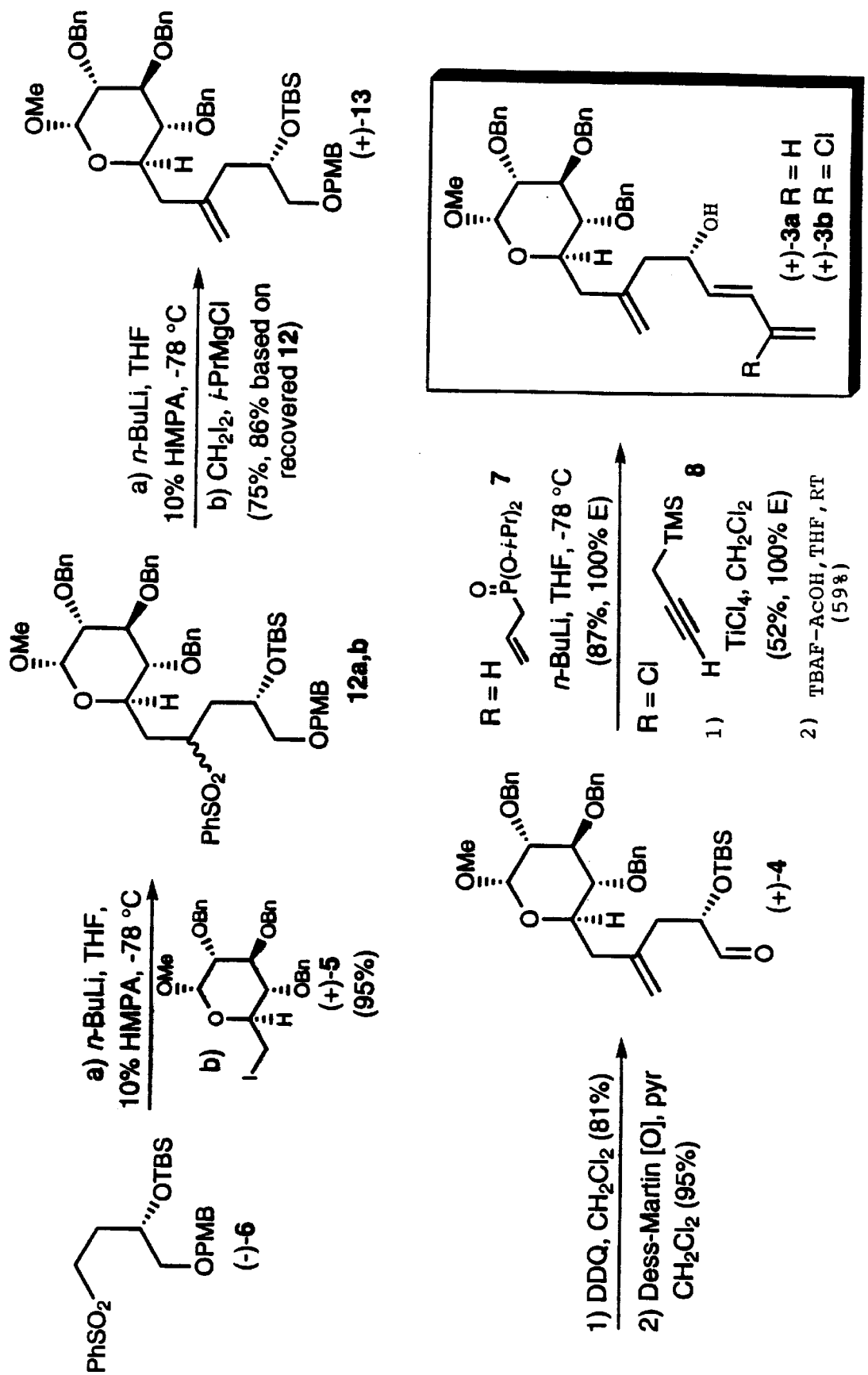
FIG. 3 shows a synthetic scheme for compounds 3a and 3b.

Coupling of model iodide (+)-5 (see, e.g., Hosokawa, et al., Synlett 1996, 351) available in five steps from methyl α-D-glucopyranoside, with sulfone (−)-6 provided 12a,b (as characterized using its infrared, 500-MHZ $^1H$ NMR, and 125-MHZ $^{13}C$ NMR spectra, as well as appropriate parent ion identification by high resolution mass spectrometry) in 95% yield as an inconsequential mixture of C(45) epimers, as shown in FIG. 3. Introduction of the methylene moiety via the Julia protocol (see, e.g., De Lima, et al, Synlett 1992, 133) then furnished (+)-13. The requisite aldehyde (+)-4 was generated by removal of the PMB ether with DDQ and Dess-martin oxidation (see, e.g., Dess, et al., J. Org. Chem. 1983, 48, 4155; Ireland, et al., J. Org. Chem. 1993, 58, 2899) of the resultant alcohol (95% yield). Olefination of (+)-4 with 7 gave exclusively the desired E diene (+)-15 in 87% yield. Desilylation of (+)-15 furnished triene (+)-3a in 95% yield. Reaction of (+)-4 with 8 and TiCl$_4$ likewise afforded the E chloro analog (+)-16 as a single isomer in 52% yield. Desilylation of (+)-16 furnished triene (+)-3b in 59% yield.

Although preferred methods are those directed to (+)-trienes 3 and compounds having like stereochemistry, those skilled in the art will recognize that the methods disclosed herein can be readily adapted to the synthesis of antipodal compounds such as, for example, (−)-trienes, and vice versa. All such synthetic methods are within the scope of the present invention.

The compounds of the invention can be admixed with carriers, excipients, and/or diluents to form novel compositions. Such compositions can be used in prophylactic, diagnostic, and/or therapeutic techniques. By administering an effective amount of such a composition, prophylactic or therapeutic responses can be produced in a human or some other type mammal. It will be appreciated that the production of prophylactic or therapeutic responses includes the initiation or enhancement of desirable responses, as well as the mitigation, cessation, or suppression of undesirable responses. The compositions of the invention are expected to find use, for example, in the inhibition of undesired cell proliferation (e.g., cancer). (See, e.g., Bai, et al., *Biochemistry* 1995, 34, 9714).

Compositions of the invention can be prepared by any of the methods well known in the pharmaceutical art, for example, as described in *Remington's Pharmaceutical Sciences* (Mack Pub. Co., Easton, Pa., 1980). The compositions can include a compound of the invention as an active ingredient in admixture with an organic or inorganic carrier or excipient suitable, for example, for oral administration. Other suitable modes of administration will be apparent to those skilled in the art. The compound of the invention can be compounded, for example, with the usual non-toxic, pharmaceutically acceptable carriers for tablets, pellets, capsules, solutions, suppositories, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The compound of the invention is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in appropriately soluble (e.g., gelatin) capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, glycerin and various like combinations thereof.

For parenteral administration, suspensions containing a compound of the invention in, for example, aqueous propylene glycol can be employed. The suspensions should be suitably buffered (preferably pH>8) if necessary and the liquid diluent first rendered isotonic. The aqueous suspensions are suitable for intravenous injection purposes. The preparation of such suspensions under sterile conditions is readily accomplished by standard pharmaceutical techniques well-known to those skilled in the art. Additionally, it is possible to administer the compounds of the invention topically and this may preferably by done by way of creams. jellies, gels, pastes, ointments and the like, in accordance with standard pharmaceutical practice.

The compounds of the invention can be employed as the sole active agent in a pharmaceutical composition or can be used in combination with other active ingredients, e.g., other agents useful in diseases or disorders.

The amount of active ingredient that is to be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, wile in other cases still larger doses may be employed without causing any harmful side effects provided that such higher doses levels are first divided into several small doses for administration throughout the day. The concentrations of the active ingredient in therapeutic compositions will vary depending upon a number of factors, including the dosage of the drug to be administrated, the chemical characteristics (e.g., hydrophobicity) of the active ingredient, and the route of administration. Typical dose ranges are from about 285 $\mu$g/kg of body weight per day in three divided doses; a preferred dose range is from about 42 $\mu$g/kg to about 171 $\mu$g/kg of body weight per day. The preferred dosage to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors well known to those skilled in the art.

Additional objects, advantages, and novel features of this invention will become apparent to those skilled in the art upon examination of the following examples thereof, which are not intended to be limiting.

All reactions were carried out in oven-dried or flame-dried glassware under an argon atmosphere, unless otherwise noted. All solvents were reagent grade. Tetrahydrofuran (THF) was freshly distilled from sodium-benzophenone under argon before use. Dichloromethane, hexamethylphosphoramide (HMPA) was freshly distilled from calcium hydride. Anhydrous pyridine and dimethylformamide were purchased from Aldrich and used without purification. n-Butyllithium and t-butyllithium were purchased from Aldrich.

Unless stated otherwise all reactions were magnetically stirred and monitored by thin layer chromatography using 0.25 mm E. Merck pre-coated silica gel plates. Flash column chromatography was performed with the indicated solvents using E. Merck silica gel-60 (230–400 mesh). Yields refer to chromatographically and spectroscopically pure compounds, unless otherwise stated.

EXAMPLE 1

Epoxide (−)-10

To a stirred suspension of NaH (60% dispersion in mineral oil, 3.24 g, 81.0 mmol) in 270 ml of anhydrous DMF at 0° C. was added R-(+)-glycidol (5.00 g, 67.5 mmol). After stirring at 0° C. for 30 minutes, PMBCl (10.57 g, 9.15 ml, 67.5 mmol) and catalytic tetrabutylammonium iodide was added. The reaction fixture was stirred at room temperature for 3.5 hours. The reaction was quenched with saturated aqueous ammonium chloride solution, extracted with ethyl acetate. The organic layer was washed with brine, dried over $MgSO_4$, filtered, and concentrated. Flash chromatography (gradient elution: 1:9 to 2:8 ethyl acetate/hexane) gave 10 (9.40 g, 72%) as colorless oil. $[\alpha]D=-3.45°$ (c 3.80 $CHCl_3$).

EXAMPLE 2

Alcohol (−)-11

To a stirred solution of methyl phenyl sulfone (15.12 g, 96.8 mmol) in 450 ml dry THF and 25 ml of dry HMPA at −50° C. was added n-BuLi (2.5 M in hexane, 38.7 ml, 96.8 mmol). After stirring at −50° C. for 20 minutes, epoxide 10 (9.40 g, 48.4 mmol) in 50 ml of dry THF was added via cannula. The reaction mixture was stirred at −50° C. for 1 hour, then slowly warmed to room temperature over 2 hours. The reaction was quenched with saturated aqueous ammonium chloride, extracted with ethyl acetate. The organic layer was washed with brine, dried over $MgSO_4$, filtered, and concentrated. Flash chromatography (gradient elution: 4:6 to 6:4 ethyl acetate/hexane) gave 11 (17.0 g, 100%) as colorless oil. $[\alpha]D=-10.9°$ (c 3.80 $CHCl_3$).

EXAMPLE 3

Epoxide (−)-6

To a stirred suspension of alcohol 11 (615 mg, 1.75 mmol) and 2,6-lutidine in (375 mg, 408 ml, 3.50 mmol) in 15 ml of dry methylene chloride at 0° C. was added TBSOTf (695 mg, 604 ml, 2.63 mmol) via syringe. The reaction fixture was stirred at 0° C. for 1 hour. The reaction was quenched with water, extracted with ether. Ether layer was washed with brine, dried over $MgSO_4$. Filtered and concentrated. Flash chromatography (2:8 ethyl acetate/hexane) gave 6 (816 mg, 100%) of product as colorless oil. $[\alpha]D=-13.0°$ (c 3.00 $CHCl_3$),

EXAMPLE 4

Sulfone 12a,b

To a stirred solution of sulfone 6 (4.604 g, 9.907 mmol) in 60 ml of dry THF under argon at −78° C. was added n-BuLi (2.5 M in hexane, 3.96 ml, 9.907 mmol) dropwise via a syringe. The resulting yellow solution was stirred at −78° C. for 30 minutes, 8 ml of HMPA was added via a syringe and stirred at −78° C. for 10 minutes. The iodide 5 (2.846 g, 4.954 mmol) in 20 ml of dry THF was added via cannula. The reaction mixture was slowly warmed to room temperature over 4 hours 20 minutes. The reaction was quenched with saturated aqueous ammonium chloride, extracted with ethyl acetate. The organic layer was washed with brine, dried over $MgSO_4$, filtered, and concentrated. Flash chromatography (gradient elution: 1:9 to 2:8 ethyl acetate/hexane) gave 12a,b (4.308 g, 95%) as colorless oil.

EXAMPLE 5

Compound (+)-13

To a stirred solution of sulfone 12a,b (862 g, 0.946 mmol) in 6 ml of dry THF and 1.2 ml of dry HMPA at −78° C. was added n-BuLi (1.6 M in hexane, 650 ml, 1.04 mmol) dropwise. The resulting orange solution was stirred at −78° C. for 45 minutes. The carbenoid was prepared independently at the same time by the following procedure: to a stirred solution of diiodomethane (760 mg, 229 ml, 2.838 mmol) in 6 ml of dry THF at −78° C. was added i-PrMgCl dropwise. The reaction mixture was stirred at −78° C. for 30 minutes. To this carbenoid mixture was added the above lithiated sulfone via cannula. The resultant yellow solution was stirred at −75° C. for 1 h, then slowly warmed to 10° C. over 4 hours. The reaction was quenched with water, extracted with ethyl acetate. The organic layer was washed with brine, dried over $MgSO_4$, filtered, and concentrated. Flash chromatography (gradient elution: 1:9 to 2:8 ethyl acetate/hexane) gave 13 (556 mg, 75%) colorless oil as well as 109 mg (13%) recovery of starting material 12a,b. For 13, $[\alpha]D=+7.8°$ (c 3.20 $CHCl_3$),

EXAMPLE 6

Alcohol (+)-14

To a stirred solution of 13 (73 mg, 0.093 mmol) in 2 ml of methylene chloride and 111 ml of water was added DDQ (43 mg, 0.186 mmol) at room temperature. The reaction mixture was stirred at room temperature for 2 hours. The reaction was quenched with saturated aqueous $NaHCO_3$, extracted with methylene chloride. The organic layer was washed with brine, dried over $MgSO_4$, filtered and concentrated. Flash chromatography (2:8 ethyl acetate/hexane) gave 14 (50 mg, 81%) as colorless oil. $[\alpha]D=+17.5°$ (c 5.25 $CHCl_3$),

EXAMPLE 7

Aldehyde (+)-4

To a stirred solution of alcohol 14 (125 mg, 0.189 mmol) in 2 ml of dry methylene chloride at room temperature was added pyridine followed by Dess-Martin periodinate (120 mg, 0.284 mmol). The reaction mixture was stirred at room temperature for 1.5 hours. The reaction was quenched with 10 ml of 1:1 saturated $NaHCO_3/Na_2S_2O_3$, extracted with ethyl acetate. The organic layer was washed with brine, dried over $MgSO_4$, filtered and concentrated. Flash chromatography (2:8 ethyl acetate/hexane) gave 4 (118 mg, 95%) as colorless oil. $[\alpha]D=+6.0°$ (c 3.95 $CHCl_3$),

EXAMPLE 8

Diene (+)-15

To a stirred solution of diisopropyl ally phosphonate 7 (188 mg 0.91 mmol) in 2 ml of dry THF at −78° C. was added n-BuLi (1.6 M in hexane, 569 ml, 0.91 mmol) dropwise via a syringe. The resulting pale yellow solution was stirred at −78° C. for 30 minutes, the aldehyde 4 (60 mg, 0.91 mmol) was then added via cannula. The reaction mixture was slowly warmed to room temperature over 5 hours 40 minutes. The reaction was quenched with saturated aqueous ammonium chloride, extracted with ether. The organic layer was washed with brine, dried over $MgSO_4$, filtered and concentrated. Flash chromatography (gradient elution:2% to 5% ethyl acetate/hexane) gave 15 (54 mg, 87%) as colorless oil. $[\alpha]D=+9.2°$ (c 0.60 $CHCl_3$),

EXAMPLE 9

Diene (+)-16

To a stirred mixture of aldehyde 4 (23 mg 0.035 mmol) and LiCl (15 mg, 0.35 mmol) in 0.5 ml of dry methylene chloride at −78° C. was added TiCl$_4$ (1.0 M in methylene chloride, 18 ml, 0.018 mmol). The resulting yellow mixture was warmed to −60° C. over 10 minutes. Propargyl trimethylsilane 8 (79 mg, 105 ml, 0.070 mmol) was then added. The reaction mixture was warmed to 4° C. over 2 hours 10 minutes. The reaction was quenched with saturated NaHCO$_3$, extracted with ethyl acetate. The organic layer was washed with brine, dried over MgSO$_4$, filtered, and concentrated. Flash chromatography (gradient elution:1:9 to 2/8 ether/hexane) gave 16 (13 mg, 52%) as colorless oil as well as 3 mg (13%) of recovery of aldehyde 4. For 16,[α]D=+11.6° (c 0.85 CHCl$_3$),

EXAMPLE 10

Triene (+)-3a

To a stirred solution of 15 (24 mg, 0.035 mmol) in 0.5 ml of dry THF was added TBAF (1.0 M in THF, 175 ml, 0.175 mmol). The reaction mixture was stirred at room temperature for 4 hours 50 minutes, diluted with ethyl acetate, washed with brine, dried over MgSO$_4$, filtered and concentrated. Flash chromatography (gradient elution: 1:9 to 2:8 ethyl acetate/hexane) gave 3a (19 mg, 95%) as colorless oil. [α]D=+26.60° (c 0.85 CHCl$_3$),

EXAMPLE 11

Triene (+)-3b

To a stirred solution of 16 (18 mg, 0.025 mmol) in 0.25 ml of dry THF was added TBAF (1.0 M in THF, 175 ml, 0.175 mmol) and acetic acid (14 ml, 0.25 mmol) (TBAF and AcOH were pre-mixed). The reaction mixture was stirred at room temperature for 44 hours, diluted with ethyl acetate, washed with brine, dried over MgSO$_4$, filtered and concentrated. Flash chromatography (gradient elution: 1:9 to 2:8 ethyl acetate/hexane) gave 3b (9 mg, 59%) as colorless oil. [α]D=+22.8° (c 0.40 CHCl$_3$),

EXAMPLE 12

Trienes (+)-3a and (+)-3b were tested for antitumor activity generally in accordance with the procedure described by Bai, et al., *Biochemistry* 1995, 34, 9714. As shown in Table I, both 3a and 3b are active against a series of human cancer cell lines.

TABLE I

Antitumor Activity (in vitro) of 3a and 3b GI$_{50}$ values in μm

|    | Pancreas-a BXPC-3 | Neuroblast SK-N-SH | Thyroid ca SW 1736 | Lung-NSC NCI-H460 | Pharynx-sq FADU | Prostate DU-145 |
|----|----|----|----|----|----|----|
| 3a | 0.44 | 0.54 | 1.2 | 0.46 | 0.47 | 0.56 |
| 3b | 5.3 | 3.6 | 9.6 | 11 | 8.3 | >16 |

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A compound of the formula:

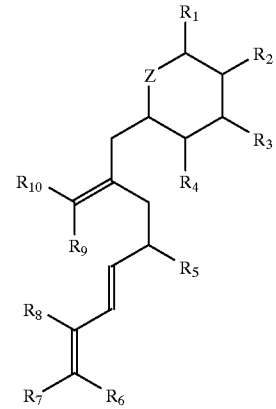

wherein:

Z is O, S or NR' where R' is H or $C_1$–$C_6$ alkyl;

$R_1$ is H, $C_1$–$C_{10}$ alkyl, =O, or OR$_A$ wherein R$_A$ is H, $C_1$–$C_{10}$ alkyl, $C_6$–$C_{14}$ aryl, $C_7$–$C_{15}$ arylalkyl, or an acid labile hydroxyl protecting group;

$R_2$, $R_3$, and $R_4$ are, independently, H, $C_1$–$C_{10}$ alkyl, or OR$_B$ wherein each R$_B$ is, independently, H, $C_1$–$C_{10}$ alkyl, $C_6$–$C_{14}$ aryl, $C_7$–$C_{15}$ arylalkyl, or an acid labile hydroxyl protecting group;

$R_5$ is H, $C_1$–$C_{10}$ alkyl, =O, or OR$_C$ wherein R$_C$ is H, $C_1$–$C_{10}$ alkyl, $C_6$–$C_{14}$ aryl, $C_7$–$C_{15}$ arylalkyl, or an acid labile hydroxyl protecting group;

$R_6$, $R_7$, $R_9$, and $R_{10}$ are, independently, H, F, Cl, Br, I, or CH(R$_D$)(R$_E$) where:
R$_D$ is H, $C_1$–$C_{10}$ alkyl, or OR$_F$;
R$_E$ is OR$_F$ or —CH$_2$—R$_F$;
R$_F$ is $C_6$–$C_{14}$ aryl, tetrahydropyranyl, furanosyl, pyranosyl, $C_3$–$C_{10}$ lactonyl or 2-pyranonyl; and $R_8$ is H, F, Cl, Br, or I.

2. The compound of claim 1 wherein Z is 0.

3. The compound of claim 1 wherein $R_1$ is OR$_A$ wherein R$_A$ is H, or $C_1$–$C_{10}$ alkyl.

4. The compound of claim 1 wherein $R_2$, $R_3$, and $R_4$ are, independently, $C_1$–$C_{10}$ alkyl or OR$_B$ wherein each R$_B$ is, independently, H, or $C_7$–$C_{15}$ arylalkyl.

5. The compound of claim 1 wherein $R_5$ is OR$_C$ wherein R$_C$ is H or an acid labile hydroxyl protecting group.

6. The compound of claim 1 wherein $R_6$, $R_7$, $R_9$, and $R_{10}$ are, independently, H.

7. The compound of claim 1 wherein $R_8$ is H or Cl.

8. The compound of claim 1 wherein said alkyl is methyl.

9. The compound of claim 1 wherein said aralkyl is benzyl.

10. The compound of claim 1 wherein: Z is O; $R_1$ is OR$_A$ wherein R$_A$ is $C_1$–$C_{10}$ alkyl; $R_2$, $R_3$, and $R_4$ are OR$_B$ wherein R$_B$ is $C_7$–$C_{15}$ arylalkyl; $R_5$ is OR$_C$ wherein R$_C$ is H or an acid labile hydroxyl protecting group; $R_6$, $R_7$, $R_9$, and $R_{10}$ are H; and $R_8$ is H or Cl.

11. The compound of claim 1 of the formula:

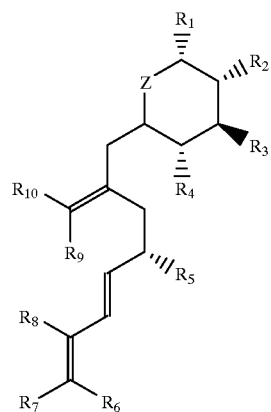

12. A composition comprising a compound according to claim 1 in admixture with and a pharmaceutically-acceptable carrier or excipients.

13. A method for inhibiting proliferation of mammalian cells selected from a group consisting of neuroblasts, cells of the pancreas, thyroid, lung, pharynx and prostate, comprising contacting the said mammalian cells with an anti-proliferative amount of a compound according to claim 1.

14. A method for treating a mammal suffering from undesired proliferation of cells selected from a group consisting of neuroblasts, cells of the pancreas, thyroid, lung, pharynx and prostate, comprising administering to said mammal with an anti-proliferative amount of a composition according to claim 12.

* * * * *